US00PP21845P2

(12) United States Plant Patent
Saul

(10) Patent No.: US PP21,845 P2
(45) Date of Patent: Apr. 5, 2011

(54) ***ANTIRRHINUM* PLANT NAMED 'SNAP DADDY YELLOW'**

(50) Latin Name: *Antirrhinum majus*
Varietal Denomination: Snap Daddy Yellow

(75) Inventor: Robert Saul, Atlanta, GA (US)

(73) Assignee: Itsaul Plants, LLC, Alpharetta, GA (US)

( * ) Notice: Subject to any disclaimer, the term of this patent is extended or adjusted under 35 U.S.C. 154(b) by 0 days.

(21) Appl. No.: 12/593,000

(22) Filed: Dec. 7, 2009

(51) Int. Cl.
*A01H 5/00* (2006.01)

(52) U.S. Cl. ..... Plt./322

(58) Field of Classification Search ..... Plt./263, Plt./322
See application file for complete search history.

*Primary Examiner* — Susan B McCormick Ewoldt
(74) *Attorney, Agent, or Firm* — Penny J. Aguirre

(57) ABSTRACT

A new cultivar of *Antirrhinum*, 'Snap Daddy Yellow', characterized by its variegated foliage with distinct cream-colored margins and soft, sea green centers, its yellow flowers, and its high degree of heat tolerance with a long blooming period in the southeast region of the U.S.

2 Drawing Sheets

Botanical classification: *Antirrhinum majus.*
Cultivar designation: 'Snap Daddy Yellow'.

BACKGROUND OF THE INVENTION

The present invention relates to a new and distinct cultivar of *Antirrhinum majus,* and will be referred to hereafter by its cultivar name, 'Snap Daddy Yellow'. The new cultivar represents a new snapdragon, a half-hardy perennial grown as an annual in containers and garden beds.

'Snap Daddy Yellow' was discovered in September of 2008 as a naturally occurring meristematic mutation of *Antirrhinum majus* 'Liberty Yellow' (not patented) that was growing in a plug that had been sown with seed of *Antirrhinum majus* seed strain Liberty Classic Mix (not patented) during bedding plant production in his nursery in Atlanta, Ga.

Asexual reproduction of the new cultivar was first accomplished by stem cuttings in October of 2008 in Atlanta, Ga. by the Inventor. The characteristics of this cultivar have been determined to be stable and are reproduced true to type in successive generations.

SUMMARY OF THE INVENTION

The following traits have been repeatedly observed and represent the characteristics of the new cultivar as observed for one year in Atlanta, Ga. These attributes in combination distinguish 'Snap Daddy Yellow' from other varieties of *Antirrhinum* known to the Inventor.

1. 'Snap Daddy Yellow' exhibits variegated foliage with distinct cream-colored margins and soft, sea green centers.
2. 'Snap Daddy Yellow' exhibits a high degree of heat tolerance and performs well in the southeast region of the U.S. where most plants of *Antirrhinum majus* die out in July and August.
3. 'Snap Daddy Yellow' has a long blooming period due to its heat tolerance.
4. 'Snap Daddy Yellow' exhibits yellow flowers, similar to its parent plant.

The parent plant of 'Snap Daddy Yellow', 'Liberty Yellow', differs from 'Snap Daddy Yellow' in having non-variegated foliage that is dark green in color. 'Snap Daddy Yellow' can be most closely compared to the cultivars 'Peppermint' (unpatented), 'Magenta' (unpatented), 'Candy Stripe' (unpatented) and 'Frosted Flames' (unpatented) which is similar to 'Snap Daddy Yellow' in having variegated foliage. 'Peppermint' differs from 'Snap Daddy Yellow' in having margins that are less defined, in having a less vigorous growth habit, and in having flowers that are rose pink in color. 'Magenta' differs from 'Snap Daddy Yellow' in having magenta pink colored flowers. 'Candy Stripe' differs from 'Snap Daddy Yellow' in having rose pink colored flowers and variegated margins that are wider and more variable. 'Frosted Flames' is a seed strain and differs from 'Snap Daddy Yellow' in having highly variable variegation (streaked) and in having flowers that are red in color.

BRIEF DESCRIPTION OF THE DRAWING

The accompanying colored photographs illustrate the overall appearance and distinct characteristics of the new *Antirrhinnum*. The photographs were taken of greenhouse grown plants of 'Snap Daddy Yellow' in Atlanta, Ga.

The photograph in FIG. 1 was taken of a plant that was grown for five months in the greenhouse, overwintered, and grown until bloom in spring and illustrates the plant habit and flowers of 'Snap Daddy Yellow'.

Figure 1:
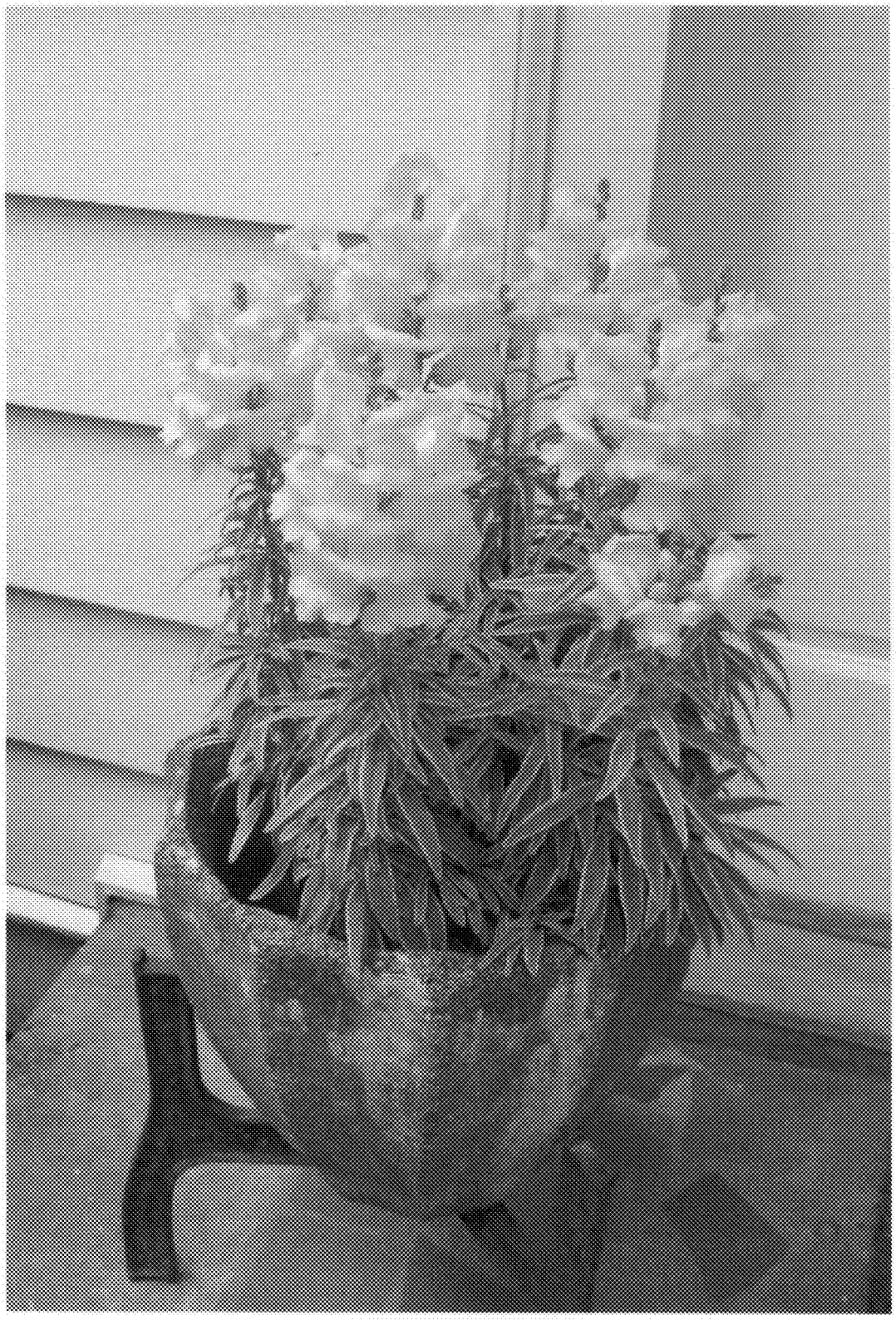
Figure 2:
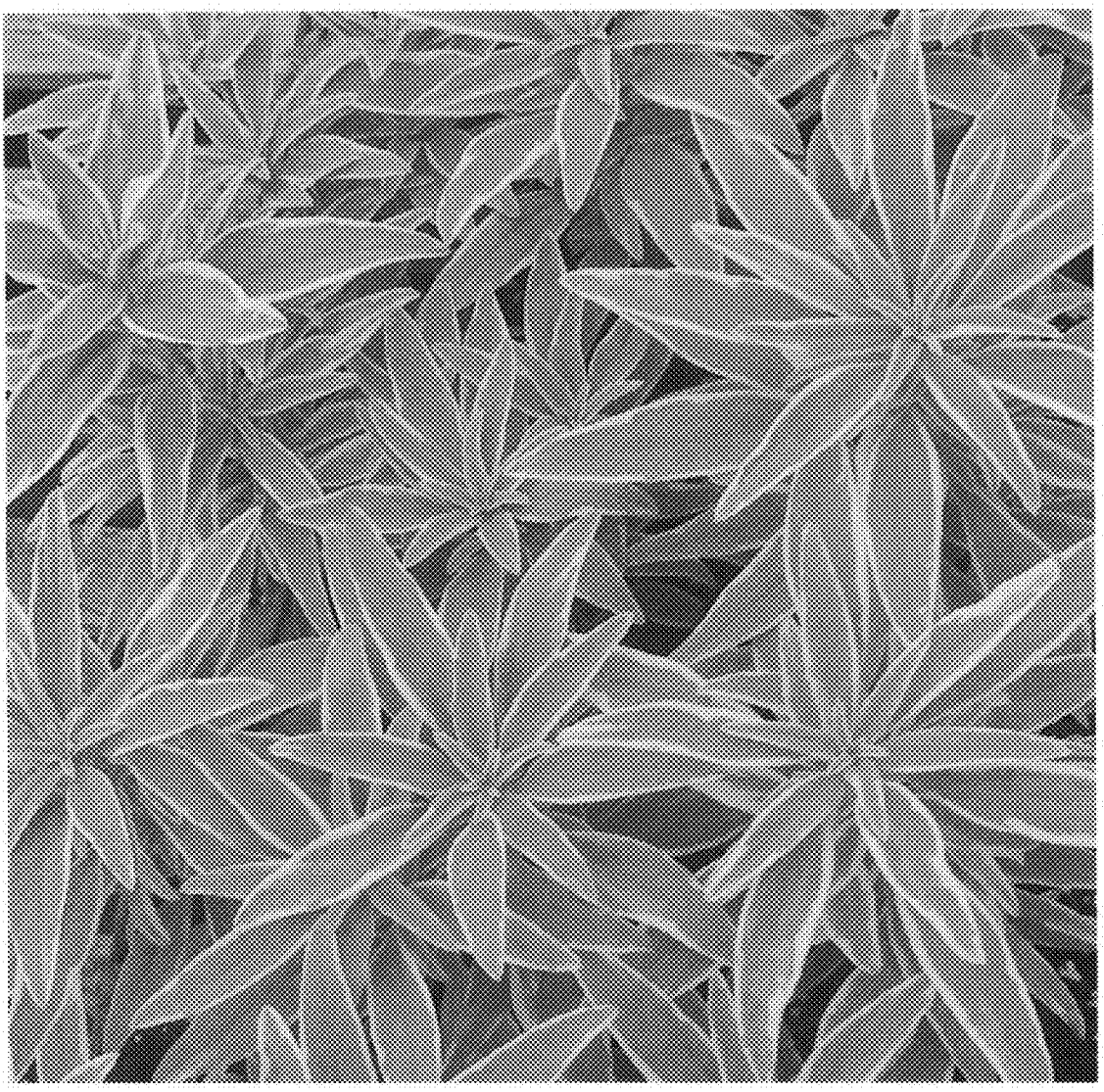

The photograph in FIG. 2 was taken of plants 8 months in age and provides a close-up view of foliage of 'Snap Daddy Yellow'. The colors in the photographs may differ slightly from the color values cited in the detailed botanical description, which accurately describe the colors of the new *Antirrhinum.*

DETAILED BOTANICAL DESCRIPTION OF THE PLANT

The following is a detailed description of plants as grown in one-gallon containers; grown for five months in the greenhouse, overwintered, and grown for another 3 months. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—March through November in Atlanta, Ga.

*Plant type.*—Half-hardy herbaceous perennial typically grown as an annual.

*Plant habit.*—Upright, dense.

*Height and spread.*—Reaches 30 to 38 cm in height and 20 to 25 cm in width.

*Cold hardiness.*—U.S.D.A. Zone 7.

*Diseases and pests.*—No susceptibility to diseases or pests has been observed.

*Root description.*—Fibrous.

Growth and propagation:

*Propagation.*—Stem cuttings.

*Root initiation and development.*—Roots initiate in about 2 weeks under mist and ambient light at 75° F., fully develop a 1.5 inch plug in about 6 weeks, and finish in a 3.5 inch pot from a 1.5 inch plug in about 5 weeks.

*Growth rate.*—Moderate to vigorous.

Stem description:

*Branch habit.*—Well branched, an average of 10 lateral branches per basal stem, an average of 7 basal stems as grown in a one-gallon container.

*Stem size.*—Main stem; average of 30 cm (including peduncle) in length and 4 mm in width lateral branches; average of 14 cm in length and 2 mm in width.

*Stem shape.*—Oval.

*Stem color.*—A blend of 138A and 138B.

*Stem surface.*—Puberulent.

*Stem aspect.*—Upright, strong, with lateral branches held from 45° to nearly upright.

*Internode length.*—Average of 6 mm.

Foliage description:

*Leaf shape.*—Lanceolate to narrowly elliptic.

*Leaf division.*—Simple.

*Leaf base.*—Attenuate.

*Leaf apex.*—Narrowly acute.

*Leaf size.*—An average of 5 cm in length and 8 mm in width.

*Leaf venation.*—Pinnate, recessed on upper surface, color on upper surface matches leaf color, color on lower surface is 194C.

*Leaf margins.*—Entire.

*Leaf attachment.*—Sessile.

*Leaf arrangement.*—Whorled.

*Leaf surface.*—Dull and finely puberulent on upper and lower surface.

*Leaf variegation pattern.*—Distinct creamy white margins about 1 mm in width with blue-green centers.

*Leaf color.*—New leaves upper surface; centers 146A, margins 4C, new leaves lower surface; centers 138B, margins 4C, mature upper and lower surface; centers 191A, margins 4D.

*Leaf number.*—An average of 21 per lateral branch 9 cm in length.

*Leaf aspect.*—Cascading downward from stem.

*Leaf internode length.*—An average of 5 mm.

Flower description:

*Inflorescence type.*—Terminal racemes of bilabiate, blooms from the base to the apex.

*Inflorescence size.*—Average of 9 cm in length and 5 cm in width.

*Lastingness of flower.*—About 5 days, not persistent.

*Flower size.*—About 3.8 cm in depth and about 2 cm in diameter.

*Flower fragrance.*—None detected.

*Flower number per inflorescence.*—An average of 9 per lateral and terminal stem.

*Peduncle.*—Oval in shape, up to 13 cm in length and an average of 2.5 mm in width, a blend of 138A and 138B in color, surface is finely puberulent, flower internode length averages about 5 mm.

*Pedicel.*—About 6.5 mm in length, about 2 mm in width, oval in shape, color a blend of 138B and 138C, surface is pubescent with glandular hairs, one leaf at base; up to 2.2 cm in length and 7 mm in width with similar characteristics to stem leaves.

*Flower buds.*—Kidney-shaped, about 2.5 cm in length and 1 cm in width, color of petal portion is a blend of 4C and 4D, calyx portion same as open flowers.

*Flower type.*—Bilabiate, held at about a 45° angle to peduncle.

*Calyx.*—Campanulate, about 7 mm in length and 9 mm in diameter, persistent but dry to 200A in color.

*Sepals.*—5, fused at base only, elliptic in shape, 4.5 mm in width and 7 mm in length broadly acute apex, margins entire, variegated with centers 138A in color and margins 155B in color, surface is highly pubescent with glandular hairs.

*Corolla features.*—Bilabiate and fused to tube, upper lip; comprised of 2 kidney-shaped lobes that are cup-like, each lobe is about 1.2 cm in width and 1.8 mm in length with rounded apex, lower lip; comprised of a 2 lobe banner and a raised center lobe with keel and crested interior, combined an average of 2.5 cm in width and 1 cm in depth, surface of both lips is puberulent to pubescent, margins of both lips are entire, tube is about 2 cm in length and 1.2 cm in with, color of outer and inner surface of upper lip and lower surface of lower lip is a blend of 4C and 4D with margins 4B, color of tube is 4D and with the area under lower lip suffused with 4B, color of inner surface of lower lip is a blend of 4B and 4C becoming 7A on keel, color of interior of lower lip and throat is NN155B with crested region that extends into tube 14B.

*Receptacle.*—Disk-shaped, gelatinous, 144A in color, about 2.5 mm in diameter and 1.5 mm in depth.

Reproductive organs:

*Gynoecium.*—1 Pistil, about 2 cm in length, 1.8 mm in width, style is 4D in color and 1.7 cm in length, stigma expanded club-shape at terminus and about 153D in color, ovary is superior, oblong in shape, 145C in color, 3.5 mm in length and 2 mm in width.

*Androcoecium.*—4 stamens, not united, about 1.9 cm in length; filament is 1.8 cm in length, <1 mm in width and N155B in color; anther is amorphously shaped, about 1.5 mm in length and 1 mm in width and N200A in color, pollen is sparse in quantity and 161D in color.

*Fruit and seed.*—Fruit; a capsule, oblong in shape with a long thin beak, an average of 1.6 cm in length (including beak 6 mm in length and 1 mm in width), color is a blend of N199D, 200A and 202B, seeds; round, spiky, about 1.2 mm in diameter, 200B in color.

It is claimed:

1. A new and distinct cultivar of *Antirrhinum* plant named 'Snap Daddy Yellow' as herein illustrated and described.

* * * * *